(12) United States Patent
Calvez et al.

(10) Patent No.: US 8,968,419 B2
(45) Date of Patent: Mar. 3, 2015

(54) PROSTHESIS COMPRISING KNITTED MATERIAL LAYERS AND METHOD OF MANUFACTURING BY ULTRASONIC WELDING

(75) Inventors: Xavier Calvez, Villefranche sur Saone (FR); Frèdèric Evrard, Pommiers (FR)

(73) Assignee: Sofradim Production (FR)

( * ) Notice: Subject to any disclaimer, the term of this patent is extended or adjusted under 35 U.S.C. 154(b) by 481 days.

(21) Appl. No.: 13/063,336

(22) PCT Filed: Sep. 10, 2009

(86) PCT No.: PCT/IB2009/007031
§ 371 (c)(1),
(2), (4) Date: Mar. 10, 2011

(87) PCT Pub. No.: WO2010/029438
PCT Pub. Date: Mar. 18, 2010

(65) Prior Publication Data
US 2011/0166494 A1 Jul. 7, 2011

(30) Foreign Application Priority Data
Sep. 11, 2008 (FR) ..................................... 08 04997

(51) Int. Cl.
*A61F 2/02* (2006.01)
*A61F 2/00* (2006.01)
(Continued)

(52) U.S. Cl.
CPC .............. *A61F 2/0063* (2013.01); *B29C 65/02* (2013.01); *B29C 65/08* (2013.01);
(Continued)

(58) Field of Classification Search
CPC ...................................................... A61F 2/0063
USPC ............. 606/151; 623/23.74, 23.75; 604/8, 9; 66/191, 192, 195, 198, 170; 428/114, 428/197; 442/305, 312–314; 28/141, 142
See application file for complete search history.

(56) References Cited

U.S. PATENT DOCUMENTS 5,456,711 A * 10/1995 Hudson ........................... 623/1.5
5,464,488 A 11/1995 Servin
(Continued)

FOREIGN PATENT DOCUMENTS

FR 2766698 A1 * 2/1999
WO WO 01/81667 11/2001
WO WO 2007/120138 10/2007

OTHER PUBLICATIONS

International Search Report PCT/IB2009/007031 dated Jan. 7, 2010.

*Primary Examiner* — Katrina Stransky

(57) ABSTRACT

The present invention relates to a prosthesis comprising at least two pieces of knitted fabric and to the method of manufacturing it using a sonotrode to perform ultrasonic welding. The prosthesis comprises at least one first piece of knitted fabric and at least one second piece of knitted fabric, which are welded together by means of a plurality of welds situated in a joining region in which at least a portion of the said first and second pieces of knitted fabric are superposed, the said first and second pieces of knitted fabric each comprising a group of yarns extending respectively in first and second directions A and B, characterized in that the said directions A and B are substantially aligned with one another in the said joining region, and each said weld in the joining region is of elongate shape with its longitudinal axis being aligned with the said directions A and B.

12 Claims, 2 Drawing Sheets

(51) Int. Cl.
*B29C 65/02* (2006.01)
*B29C 65/08* (2006.01)
*B29C 65/00* (2006.01)
*D04B 21/12* (2006.01)
*D06H 5/00* (2006.01)
*B29L 31/00* (2006.01)

(52) U.S. Cl.
CPC ............ *B29C 66/1122* (2013.01); *B29C 66/21* (2013.01); *B29C 66/232* (2013.01); *B29C 66/43* (2013.01); *B29C 66/729* (2013.01); *B29K 2313/00* (2013.01); *B29L 2031/7532* (2013.01); *D04B 21/12* (2013.01); *D06H 5/00* (2013.01); *D10B 2501/0632* (2013.01); *D10B 2509/08* (2013.01); *B29C 66/8322* (2013.01); *B29C 66/81427* (2013.01); *B29C 66/81433* (2013.01)
USPC ........................................ 623/23.74; 606/151

(56) References Cited

U.S. PATENT DOCUMENTS

| | | | |
|---|---|---|---|
| 6,113,623 | A | 9/2000 | Sgro |
| 6,120,539 | A * | 9/2000 | Eldridge et al. ............ 623/11.11 |
| 6,287,316 | B1 * | 9/2001 | Agarwal et al. ................ 606/151 |
| 7,614,258 | B2 * | 11/2009 | Cherok et al. ................... 66/192 |
| 2002/0013590 | A1 * | 1/2002 | Therin et al. ................... 606/151 |
| 2003/0100954 | A1 * | 5/2003 | Schuldt-Hempe et al. 623/23.72 |
| 2004/0054376 | A1 * | 3/2004 | Ory et al. ....................... 606/151 |
| 2005/0070930 | A1 * | 3/2005 | Kammerer .................... 606/151 |
| 2006/0016571 | A1 * | 1/2006 | Silakoski .................... 162/358.2 |
| 2006/0195010 | A1 | 8/2006 | Arnal et al. |
| 2007/0055093 | A1 * | 3/2007 | Beraud ............................ 600/30 |
| 2007/0270742 | A1 * | 11/2007 | Guetty .................... 604/103.05 |
| 2009/0326565 | A1 * | 12/2009 | Trabucco et al. ............. 606/151 |

* cited by examiner

PROSTHESIS COMPRISING KNITTED MATERIAL LAYERS AND METHOD OF MANUFACTURING BY ULTRASONIC WELDING

CROSS-REFERENCE TO RELATED APPLICATIONS

This application is a U.S. National Stage Application filed under 35 U.S.C. §371(a) of International Application No. PCT/IB2009/007031, filed Sep. 10, 2009, which claims the benefit of and priority to French Application 08/04997 filed Sep. 11, 2008, the entire contents of which are incorporated by reference herein.

The invention relates to a prosthesis comprising at least two pieces of knitted fabric and to the method of manufacturing it which employs a sonotrode to perform ultrasonic welding.

Numerous surgical operations require the use of textile implants. Very often, the central part of such textile implants is intended to be positioned in the region of organs and may be in contact therewith in order to support them while the lateral parts are attached to stable anatomical elements such as the abdominal wall, the obturating membrane, the sacral promontory, the sacro-sciatic ligaments or the pubic bone, for example using staples, sutures or simple tissue anchorage.

In the known way, such textile implants have to meet numerous requirements and, in particular, each textile implant has to have suitable mechanical strength in at least two directions, has to be biocompatible, flexible and exhibit a certain degree of elasticity. These textile implants preferably have to be porous and non-aggressive in their central part supporting the organ. Very often, these textile implants additionally have to be able to be sutured. Porosity is essential in order to encourage tissue colonization and/or in order to allow the textile implant to be absorbed into the organism in which it is implanted. Finally, it is of primordial importance that these textile implants conform to the anatomy of the region of the patient in which they are implanted.

In order to adapt the shape of a textile implant to suit the anatomy of an implantation site, it may be necessary to produce this implant in the form of an assembly of several pieces of knitted fabric. It is known practice to obtain such assemblies by stitching the said pieces of knitted fabric together, as is, for example, the case of the prosthetic knitted fabric described in Patent Application WO01/81667.

The seams are generally stitched by hand by an operator, and this does not always allow satisfactory repeatability to be obtained in terms of the breaking strength of the said seams. Now, like any material for surgical use, it is essential that the mechanical properties of a textile implant be clearly defined, with satisfactory repeatability.

It is an object of the present invention to provide textile implants that meet the specific requirements of prosthetic knitted fabrics, as recalled hereinabove, particularly those of porosity, and that can be obtained by a method of manufacture that ensures good repeatability in the mechanical properties, most especially in terms of the breaking strength. It is another object of the present invention to provide textile implants obtained with shorter production times and lower production costs.

The present invention proposes a prosthesis comprising at least one first piece of knitted fabric and at least one second piece of knitted fabric, the said first and second pieces of knitted fabric being welded together by means of a plurality of welds situated in a joining region in which at least a portion of the said first piece of knitted fabric and at least a portion of the said second piece of knitted fabric are superposed, the said first piece of knitted fabric comprising a first group of yarns extending in a first direction A and the said second piece of knitted fabric comprising a second group of yarns extending in a second direction B, characterized in that the said first and second directions A and B are substantially aligned with one another in the said joining region, and each said weld in the joining region is of elongate shape with its longitudinal axis aligned with the said first and second directions A and B.

The prosthesis according to the invention thus exhibits good repeatability in terms of breaking strength because aligning the longitudinal axis of the welds with the directions A and B ensures an even distribution of material along the welds; this arrangement thus makes it easier to control the shape of the welds, something that is essential in obtaining a good distribution of load when the prosthesis is subjected to tensile stresses. The prosthesis according to the invention also retains porosity and flexibility in the joining region that are compatible with good adaptation within the organism, because assembly by discrete welds avoids rendering the joining region non-porous. Such a prosthesis is obtained with production times and production costs that are respectively shorter and lower by comparison with a similar prosthesis in which the first and second pieces of knitted fabric are assembled by stitched seams.

The present invention also relates to textile implants comprising at least two pieces of knitted fabric secured by welding, in particular by ultrasonic welding. The textile implants of the present invention may, for example, be prosthetic knitted fabrics forming two flaps that are superposed at least locally and intended to repair inguinal hernias.

In one embodiment of the invention, the said welds are spaced over the said joining region: the presence of the spaces makes it possible to maintain flexibility in the said joining region. The flexibility of the said joining region may be enhanced by increasing the number of discrete welds.

In one embodiment of the invention, the said first group of yarns constitutes at least one first pillar stitch weave.

In one embodiment of the invention, the said second group of yarns constitutes at least one second pillar stitch weave.

In one embodiment of the invention, the said first and second groups of yarns respectively constitute at least one first pillar stitch weave and one second pillar stitch weave and the said pillar stitches of the said first and second pillar stitch weaves are superposed. As a preference then, the spacings between the said pillar stitches of the said first and second pillar stitch weaves are superposed. Superposing the pillar stitches of the said first and second pillar stitch weaves makes it easier to position and align the two pieces of knitted fabric and to increase the density of material locally in the region of the pillar stitches. This locally increased density of material in the region of the pillar stitches makes welding easier. The welds thus produced have better repeatability in terms of their breaking strength.

In this embodiment of the invention, and as an even greater preference, at least one pillar stitch of the first pillar stitch weave and at least one pillar stitch of the second pillar stitch weave are welded together in the joining region.

In embodiments, not all of the pillar stitches of the first and second pieces of knitted fabric are welded together in the joining region so that at least one pillar stitch of each of the pieces of knitted fabric is not involved in one of the welds. This makes it possible to maintain a better flexibility of the prosthesis in the joining region.

In one embodiment of the invention, the said welds are sonic welds, in particular ultrasonic welds. In the present application, by "ultrasonic" or "ultrasound" is meant vibrations (or oscillations) having a frequency equal or greater than 20,000 Hz. The sonic, in particular ultrasonic, welds are performed quickly and allow time to be saved by comparison with stitching a seam and offer very good repeatability. In addition, sonic, in particular ultrasonic, welds make it possible to avoid any addition of material that is often responsible for patient discomfort.

In one embodiment of the invention, the said first and second pieces of knitted fabric may further be superposed in a region other than the said joining region and the said first and second pieces of knitted fabric may delimit an orifice suited to the passage of a bodily vessel or duct. A prosthesis according to the invention is, for example, suited to the repair of inguinal hernias.

In one embodiment of the invention, at least the said second piece of knitted fabric further comprises, on one of its faces, protruding picot bristles obtained by forming external plush loop stitches in the said piece of knitted fabric then by partially fusing the yarn of the said plush loops. Such picots have the advantage of dispensing with an additional operation whereby the practitioner has to join the two pieces of knitted fabric together, thus bringing greater speed, simplicity and firmness of placement.

The present disclosure also relates to a sonotrode intended to weld together, in particular using vibrations equal or greater than 20,000 Hz, at least two pieces of knitted fabric in combination with an anvil, the said sonotrode comprising a contact surface intended to press against the said pieces of knitted fabric at the time of welding, the said contact surface comprising a plurality of reliefs, each relief being of elongate shape, the reliefs being mutually parallel. A sonotrode such as this allows welds to be produced along the said groups of yarns.

In one embodiment of the sonotrode, the reliefs all have the same width and are all positioned at uniform spacings. Preferably then, the width of the said reliefs and the spacing of the said reliefs are chosen so as to make it possible to obtain prostheses for which at least one pillar stitch of the first pillar stitch weave and at least one pillar stitch of the second pillar stitch weave are welded together and for which the said welds are spaced apart in the said joining region in such a way as to maintain the flexibility of the said joining region.

Finally, the present invention also relates to a method of manufacturing a prosthesis according to the present invention using a sonotrode and an anvil, said sonotrode being intended to weld together at least said two pieces of knitted fabric in combination with the anvil, said sonotrode comprising a contact surface intended to press against the said pieces of knitted fabric at the time of welding, the said contact surface comprising a plurality of reliefs, each relief being of elongate shape, the reliefs being mutually parallel, said method of manufacturing comprising the following steps:
  a) positioning the said first and second pieces of knitted fabric on the said anvil in such a way that at least a portion of the said first piece of knitted fabric and at least a portion of the said second piece of knitted fabric are superposed at a joining region;
  b) pressing the said contact surface of the sonotrode onto the said joining region so as to clamp the said first and second pieces of knitted fabric between the said anvil and the said sonotrode;
  c) simultaneously applying a pressure force to the said joining region and imparting oscillations at ultrasound frequencies to the sonotrode.

In particular, in step a), said first and second pieces of knitted fabric are positioned in such a way that the respective directions A and B of their respective groups of yarns are substantially aligned with one another.

Thus, the method according to the present invention makes it possible to improve the repeatability in terms of the breaking strength of the prosthesis comprising an assembly of two pieces of knitted fabric. A method such as this also makes it possible to avoid costly training of the operators who are to implement it, unlike an assembly whereby the said pieces of knitted fabric are stitched together.

The Applicant Company has thus succeeded in halving the time it takes for an operator to assemble the pieces of knitted fabric by comparison with the time needed to assemble the said pieces of knitted fabric using stitched seams.

The invention will be clearly understood with the aid of the following description given by way of nonlimiting example, with reference to the attached drawings which schematically depict:

Figure 1:
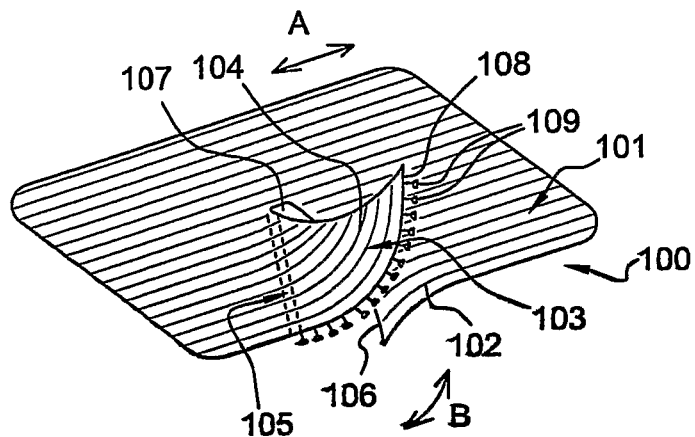
FIG. 1 depicts a perspective view of a prosthesis according to the invention with a second piece of knitted fabric moved aside in order to show the structure and shape of the prosthesis.

FIG. 1 depicts a prosthesis 100 according to the invention, in perspective. It comprises a first piece of knitted fabric 101 comprising a first group of yarns 102 constituting a first pillar stitch weave and extending substantially in a first direction indicated by an arrow A. The prosthesis 100 comprises a second piece of knitted fabric 103 comprising a second group of yarns 104 constituting a second pillar stitch weave and extending substantially in a second direction indicated by an arrow B. For example, the said groups of yarns (102, 104) constitute pillar stitches. The pillar stitch weaves that are weaves that are conventional in the field of textiles and the methods of obtaining them are well known to those skilled in the art: they will therefore not be detailed any further hereinbelow. The yarns that constitute the prosthesis 100 according to the invention, and particularly the first and second groups of yarns (102, 104) may be made of any biocompatible material. In one exemplary embodiment of the invention, at least some of the yarns that constitute the prosthesis 100 are made of a hot-melt material. Examples of hot-melt materials that can be used for the yarns of the prosthesis are polypropylene, polyester, polylactic acid and mixtures thereof.

The first and second pieces of knitted fabric (101 103) are joined together at a joining region 105 where they are partially superposed. These first and second pieces of knitted fabric (101, 103) are assembled in such a way that they can be partially superposed in a region other than the said joining region 105. The prosthesis 100 is, for example, of a shape suited to the repair of inguinal hernias and for this reason has a slot 106 and an orifice 107 for the passage of the spermatic cord when the prosthesis 100 is being implanted. The face 108 of the second piece of knitted fabric 103, which face is intended to come into contact with the first piece of knitted fabric 101, is provided with projecting picot bristles 109 obtained by forming external plush loop stitches in the said second piece of knitted fabric 103 then by partially fusing the yarn of the said plush loops. One way of obtaining such picot bristles is described for example in Patent Application WO 01/81667A. These picot bristles 109 are intended to engage in the stitches and between the yarns of the knitted fabric of the first piece of knitted fabric 101 thus locking the second piece of knitted fabric 103 to the first piece of knitted fabric 101.

Figure 2:
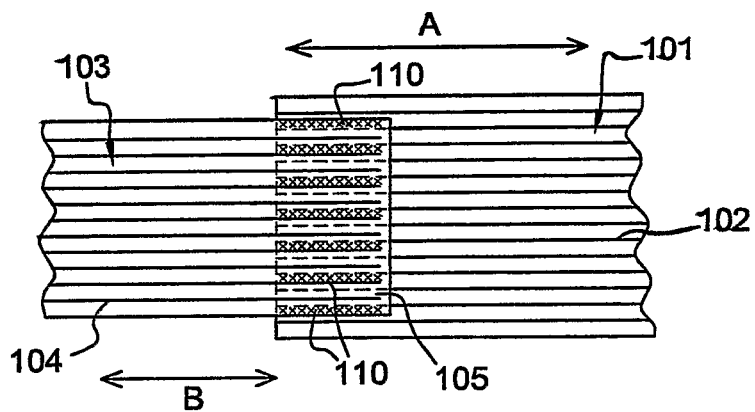
FIG. 2 depicts a schematic view of the joining region of the prosthesis depicted in FIG. 1.

FIG. 2 depicts a schematic view of the joining region 105 of the prosthesis 100 depicted in FIG. 1. The first and second pieces of knitted fabric (101, 103) are assembled together with one another by means of a plurality of mutually parallel welds 110 distributed over the said joining region 105. The first and second pieces of knitted fabric (101, 103) are assembled in such a way that the said first and second directions A and B are substantially aligned in the said joining region 105. For preference, the pillar stitches of the said first pillar stitch weave are superposed with the said pillar stitches of the second pillar stitch weave. The said welds 110 are of elongate shape, their longitudinal axis being aligned with the said first and second directions A and B, and they are spaced apart, for example with a uniform spacing, over the said joining region 105 so as to maintain the flexibility of the said joining region 105. The distribution of the welds is such that at least one pillar stitch of the first pillar stitch weave and at least one pillar stitch of the second pillar stitch weave are welded together in the joining region. As a preference, not all of the pillar stitches of the first and second pieces of knitted fabric (101, 103) are welded together in the joining region so that at least one pillar stitch, in embodiments several pillar stitches, for example from 10 to 50% of the pillar stitches, of each of the pieces of knitted fabric (101, 103) is(are) not involved in one of the welds 110; this makes it possible to maintain the flexibility in the joining region 105. The Applicant Company has thus determined that the tear strength of the prosthesis 100 is more repeatable and reproducible by comparison with a prosthesis in which stitched seams are used in place of the welds 110.

Figure 3:
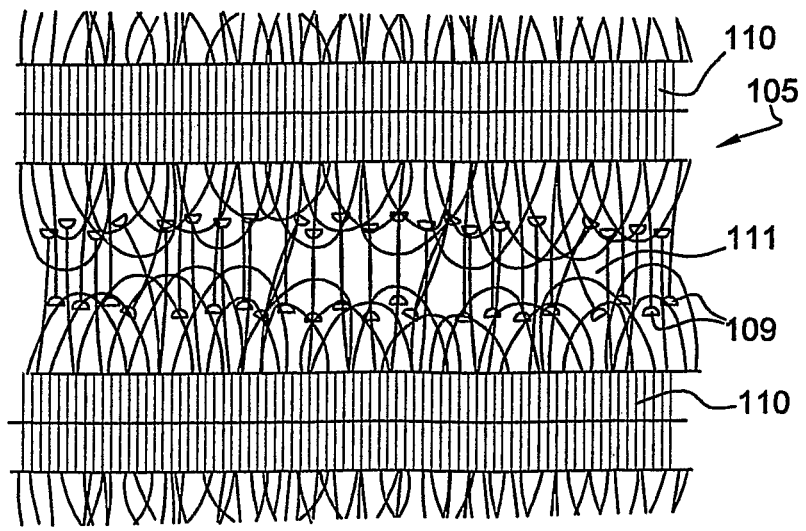
FIG. 3 depicts a detailed view of the joining region depicted in FIG. 2.

FIG. 3, which depicts an enlarged schematic view of the joining region 105, shows the picot bristles 109 which are preserved by the spacing of the welds 110 produced in the joining region 105. The presence of these picot bristles 109 has the advantage of retaining the grippy nature of the piece of knitted fabric 103, even in the joining region 105. FIG. 3 also shows that the prosthesis 100 maintains a porosity in the joining region 105 because of the presence of openings 111 or voids between those yarns that have not been welded: such a porosity maintains the capability of the prosthesis to allow cell colonization, even in the joining region 105.

Figure 4:
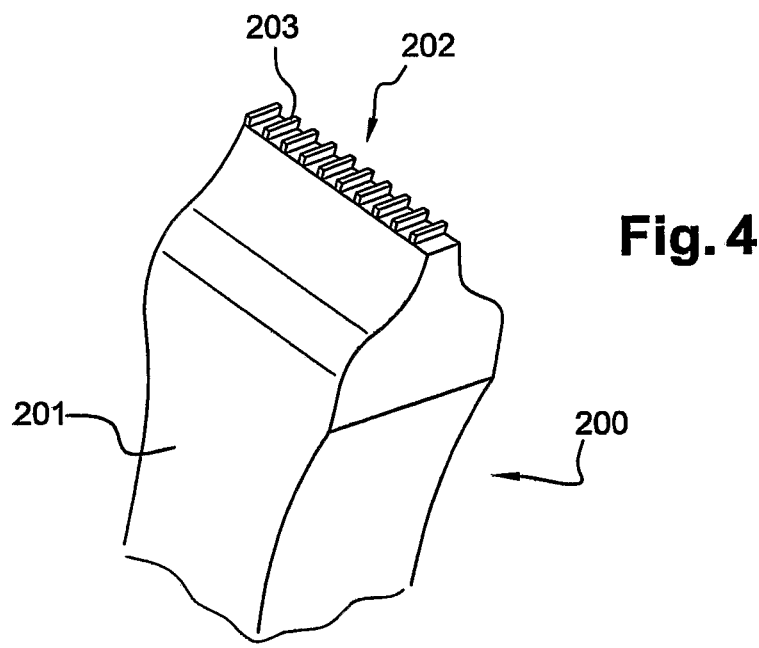
FIG. 4 depicts a perspective view of a sonotrode suitable for the method of the invention.

FIG. 4 depicts a partial view of a sonotrode 200 suitable for the manufacturing method of the present invention. The sonotrode 200 comprises a body 201 made of titanium, for example, comprising at its end a contact surface 202, for example of rectangular shape, equipped with a plurality of reliefs 203. As FIG. 4 shows, the reliefs 203 are of elongate shape, for example rectangular, and are mutually parallel. For preference, the direction of the longitudinal axes of the reliefs 203 is chosen to be perpendicular to the direction of the longitudinal axis of the contact surface 202 of the sonotrode 200. The sonotrode 200 has uniformly spaced reliefs 203. The welds 110 produced using the sonotrode 200 are the result of contact between the knitted fabric and the said reliefs 203. As a result, the said welds 110 have substantially the same shape and the same spacing as the reliefs 203.

Figure 5:
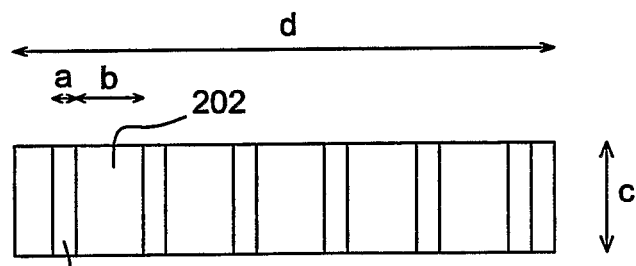
FIG. 5 depicts a front view of the contact surface of the sonotrode depicted in FIG. 2.

FIG. 5 depicts a front view of the contact surface 202 featuring the dimensions of the contact surface 202 and of the reliefs 203 for one exemplary embodiment of the invention. Thus, the sonotrode 200 has a rectangular contact surface 202 of width c, length d and with reliefs 203 of a width a, uniformly spaced apart by a distance b. For example, the parameters a, b, c and d have respective values of 1 mm, 2.5 mm, 8 mm and 36 mm. The value of a is chosen to avoid two adjacent pillar stitches on one and the same piece of knitted fabric becoming involved in the same weld 110.

Figure 6:
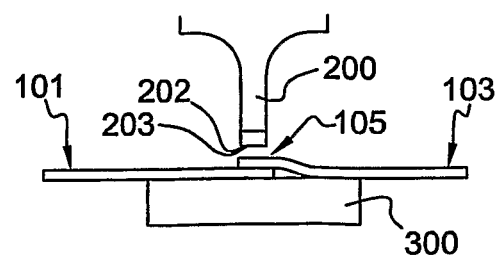
FIG. 6 depicts a schematic view of the positioning of the pieces of knitted fabric which are intended to be welded together to form a prosthesis according to the invention using the method of the invention.

FIG. 6 shows how the method according to the invention is implemented using a sonotrode 200 according to the invention with an anvil 300, made of aluminium for example, to assemble two pieces of knitted fabric (101, 103) in order to manufacture a prosthesis 100. A first piece of knitted fabric 101 and a second piece of knitted fabric 103 are superposed at a joining region 105 and positioned on the anvil 300 in such a way that the respective directions A and B of their respective groups of yarns are substantially aligned with one another. The contact surface 202 of the sonotrode 200 is brought into vertical alignment with the joining region 105 before being brought into contact with the joining region 105. The relative positioning of the pieces of knitted fabric (101, 103) and of the contact surface is chosen so as to bring the reliefs 203 into vertical alignment with the chosen locations of the welds 110 that are to be created. Thus, when the sonotrode 200 is brought into contact with the joining region 105, the reliefs 203 coincide with the desired locations of the welds 110. For preference, the lengths a, b, c and d and the positioning are chosen so that the reliefs 203, and therefore the welds 110, coincide with at least one pillar stitch of each of the pillar stitch weaves of the said pieces of knitted fabric (101, 103). To make the relative positioning of the elements easier, the anvil 300 has, for example, a predefined recessed or raised shape so that the pieces of knitted fabric (101, 103) are positioned correctly with respect to the reliefs 203.

In order to implement the method according to the present invention, the first and second pieces of knitted fabric (101, 103) are positioned as described hereinabove on the anvil 300 then the contact surface 202 of the sonotrode 200 is brought into contact with the joining region 105. Pressure is then applied between the sonotrode 200 and the anvil 300. Mechanical vibrations applied at an ultrasonic frequency are then applied to the sonotrode 200. The energy involved makes it possible to create a plurality of welds 110 by localized fusing of the fibres of the pieces of knitted fabric (101, 103). To employ the method according to the invention, it is preferable for at least some of the yarns contained in the pieces of knitted fabric that are to be assembled be hot-melt yarns. Examples of hot-melt materials that can be used for the yarns of the pieces of knitted fabric are polypropylene, polyester, polylactic acid and mixtures thereof.

The sonotrode 200 is finally raised so that the prosthesis 100 comprising the said pieces of knitted fabric (101, 103) assembled by means of welds 110 can be recovered.

This then yields a prosthesis 100 that exhibits a porosity, that is to say that comprises openings 111 or voids, and a flexibility that is satisfactory for surgical use and that is furthermore manufactured by a method which ensures both good repeatability in terms of the mechanical properties, particularly in terms of breaking strength, and also reduces the production time by comparison with a method of manufacturing a similar prosthesis which is assembled using stitched seams.

The invention claimed is:

1. A prosthesis comprising at least one first piece of knitted fabric and at least one second piece of knitted fabric, the first and second pieces of knitted fabric welded together by means of a plurality of welds situated in a joining region in which at least a portion of the first piece of knitted fabric and at least a portion of the second piece of knitted fabric are superposed, the first piece of knitted fabric comprising a first group of yarns constituting at least one first pillar stitch weave extending in a first direction A and the second piece of knitted fabric comprising a second group of yarns constituting at least one second pillar stitch weave extending in a second direction B, characterized in that the first and second directions A and B are substantially aligned with one another in the joining region, and each weld in the joining region is of elongate shape with its longitudinal axis aligned with the first and second directions A and B, wherein pillar stitches of the first and second pillar stitch weaves are superposed and at least one pillar stitch of the first pillar stitch weave and at least one pillar stitch of the second pillar stitch weave are welded together in the joining region.

2. A prosthesis according to claim 1, wherein the welds are spaced over the joining region.

3. A prosthesis according to claim 1, wherein spacings between the first and second pillar stitch weaves are superposed.

4. A prosthesis according to claim 1, wherein not all of the pillar stitches of the first and second pieces of knitted fabric are welded together in the joining region so that at least one pillar stitch of each of the pieces of knitted fabric is not involved in one of the welds.

5. A prosthesis according to claim 1, wherein the welds comprise sonic welds.

6. A prosthesis according to claim 1, wherein the welds comprise ultrasonic welds.

7. A prosthesis according to claim 1, wherein the first and second pieces of knitted fabric are superposed in a region other than the said joining region and the said first and second pieces of knitted fabric delimit an orifice suited to a passage of a bodily vessel or duct.

8. A prosthesis according to claim 1, wherein at least the second piece of knitted fabric further comprises, on at least one face, protruding picot bristles obtained by forming external plush loop stitches in the second piece of knitted fabric then by partially fusing the yarn of the plush loops.

9. A prosthesis according to claim 1, wherein the joining region maintains a porosity that allows tissue colonization.

10. A prosthesis according to claim 9, wherein the joining region maintains a flexibility to conform to an anatomy of a region in a patient in which the prosthesis may be implanted.

11. A prosthesis according to claim 1, wherein the welds are uniformly spaced over the joining region.

12. A prosthesis according to claim 1, wherein not all of the pillar stitches of the first and second pieces of knitted fabric are welded together in the joining region so that 10-50% of the pillar stitches are not involved in one of the welds.

* * * * *